United States Patent [19]

Le Page et al.

[11] 4,244,806
[45] Jan. 13, 1981

[54] PROCESS FOR CONVERTING C4 OLEFINIC CRACKING CUTS TO ALKYLATE AND GASOLINE

[75] Inventors: Jean-François Le Page, Rueil Malmaison; Jean Cosyns, Maule; Jean Miquel, Paris; Bernard Juguin, Rueil Malmaison, all of France

[73] Assignee: Institut Francais du Petrole, Rueil Malmaison, France

[21] Appl. No.: 25,630

[22] Filed: Mar. 30, 1979

[30] Foreign Application Priority Data

Mar. 31, 1978 [FR] France .............................. 78 09639

[51] Int. Cl.³ .............................................. C10G 69/12
[52] U.S. Cl. ........................................ 208/49; 208/71; 208/80; 585/255; 585/304; 585/332

[58] Field of Search .............................. 208/49, 71, 80; 585/255, 304, 332

[56] References Cited

U.S. PATENT DOCUMENTS

| 2,332,563 | 10/1943 | Egloff ..................................... 208/71 |
| 2,438,456 | 3/1948 | Russell et al. .......................... 208/71 |
| 3,309,421 | 3/1967 | Kirk et al. ............................. 585/255 |

*Primary Examiner*—Herbert Levine
*Attorney, Agent, or Firm*—Millen & White

[57] ABSTRACT

A $C_4$ olefinic cracking cut is subjected first to catalytic polymerization and then to fractionation: the resultant isobutene dimers and trimers fraction is hydrogenated, while the remainder is alkylated. The resultant product is a gasoline of high isooctane content.

14 Claims, 1 Drawing Figure

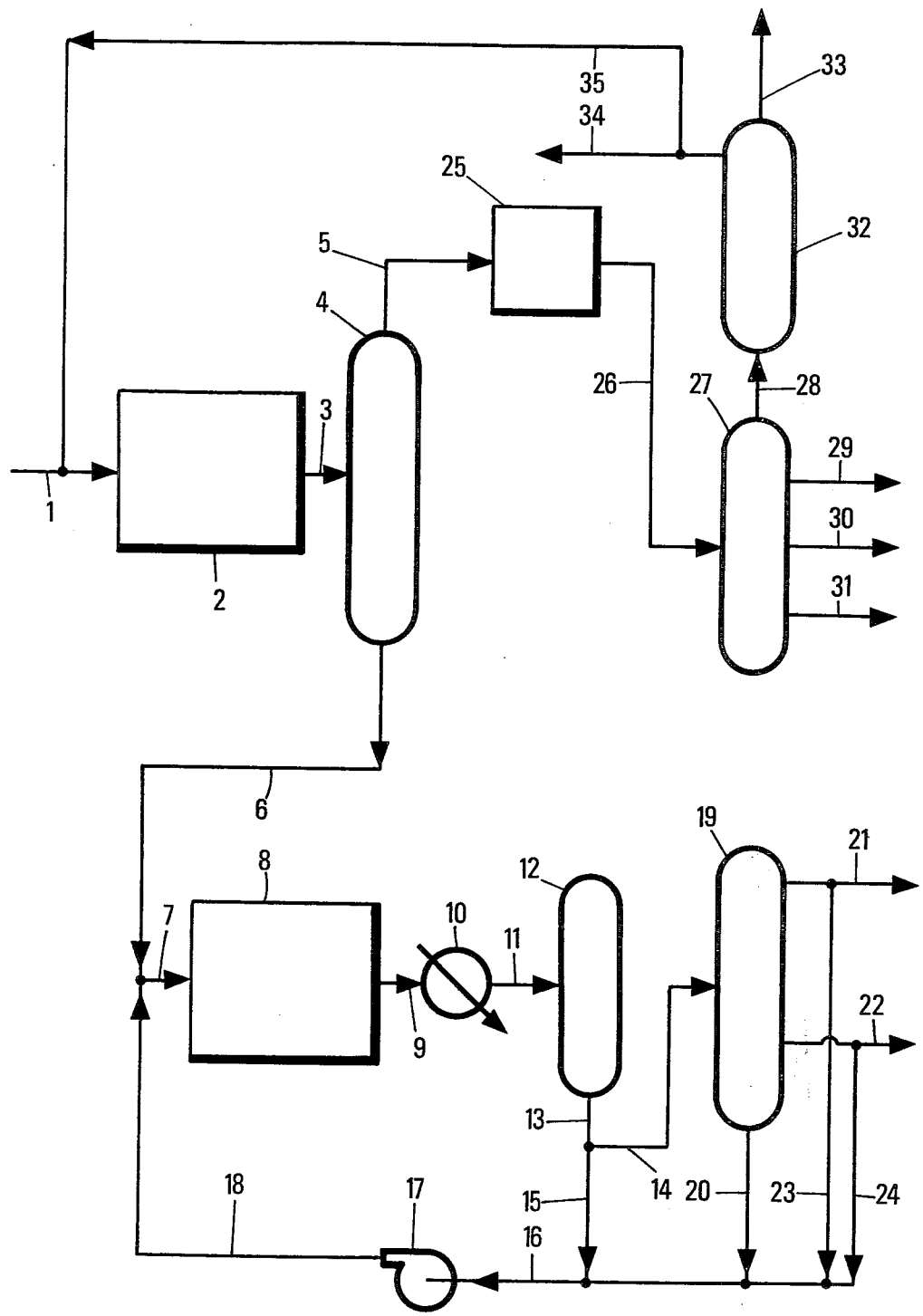

PROCESS FOR CONVERTING $C_4$ OLEFINIC CRACKING CUTS TO ALKYLATE AND GASOLINE

The development of cracking units which can be expected in the next years will put on the market an excess of isobutane, normal butenes and isobutene for which new users are to be found.

The upgrading process of the invention consists of alkylating olefins with isobutane in order to increase the gasoline yield. However, when alkylated, isobutene does not behave so favorably as the butenes to produce gasoline of high octane rating, since the research (clear) octane numbers of butene alkylates are higher than those of isobutene alkylates.

The present process, which conforms to the invention, comprises a first polymerization step through which the content of isobutene decreases due to its conversion to dimers and trimers. Fractionation follows, according to the process, in order to obtain both a cut which is thereafter alkylated and a cut which is thereafter hydrogenated to yield a gasoline fraction.

The invention has thus for object a process which comprises, in a first step, the selective conversion by polymerization of isobutene from the $C_4$ cut, constituting the feed charge, to isobutene $C_8$ dimers and $C_{12}$ trimers with a minimum conversion of the normal butenes of the feed charge; then, in a second step, the mixture discharged from the polymerization step is divided into two fractions: a first fraction comprises in major part butane, isobutane and butenes, and a second fraction comprises essentially isobutene dimers and trimers. In a third step, the first fraction is fed to an alkylation zone, whereas the second fraction is hydrogenated essentially to isooctane and isododecane; this hydrogenated gasoline fraction is upgraded as gasoline of very high octane rating (RON clear $\geq 100$). Optionally and preferably the two outflows from the alkylation, and hydrogenation steps are admixed and used as gasoline.

The process conforming to the invention is illustrated by the accompanying drawing. In a first step, the olefinic $C_4$ cut is fed through line 1 to the polymerization zone 2 under such conditions that isobutene reacts up to conversion rates higher than 90% by weight, while the aggregate converson of the normal butenes (1-butene and cis and trans 2-butenes) remains lower than 10% by weight. Resultant gasoline comprises, among others, a mixture of dimers and trimers in respective proportions of 60 to 80% by weight of dimers and 20 to 40% by weight of trimers. The operation is effected in the following conditions:

space velocity (VVH): 0.5 to 5 (in liters of the feed charge per liter of catalyst and per hour);
pressure: 25 to 60 bars;
temperature: 100° to 180° C.

Taking into account the high exothermicity of the conversion it is preferably that the isobutene content of the charge be not in excess of about 35% by weight, since otherwise, it would be necessary to dilute it, for example with butane or isobutane and/or, for example, with a butane fraction recovered through line 35 from an alkylation zone 25 and fractionation zone 27 as defined below. This recycled butane fraction is fed to the polymerization zone 2, either at the top of the reactor or at intermediate points of the catalyst bed so as to avoid too high a temperature increase.

The polymerization catalyst is either fluorinated alumina or boron-alumina or, preferably, silica-alumina whose silica content is from 60 to 95% by weight and, preferably, and 70 to 90%. These catalysts are used as balls, extrudates or tablets whose equivalent diameter is, for example, from about 2 to 5 mm.

At the outlet of the polymerization zone, all the outflows, i.e. unconverted butenes, unconverted isobutene, isobutene dimers and trimers, butane and dilution butane, isobutane and the like, are fed through line 3 to a fractionation zone 4 from which are discharged, through duct 5, a first fraction mainly comprising butane, isobutane, isobutene and butenes and, through duct 6, a second fraction mainly comprising isobutene dimers and trimers. The second fraction is supplied, through duct 7, to a hydrogenation zone 8.

The operating conditions for the hydrogenation in zone 8 are as follows:
VVH: 1 to 5
Pressure: 25 to 60 bars
Temperature: 150° to 220° C.

The hydrogenation outflow, discharged through duct 9, is passed to cooler 10 and supplied, through duct 11, to the separation vessel 12, wherefrom it is conveyed, through duct 14, to the distillation column 19.

Too high a temperature increase, due to the strongly exothermic nature of the reaction, may be avoided by recycling liquid from the separation vessel 12 (and/or from the bottom of the distillation column 19) to the top of the hydrogenation catalyst bed, through ducts 13, 15, 16, 20, through pump 17 and line 18.

The hydrogen gas to be used for hydrogenation may be pure hydrogen or hydrogen obtained from a steam-cracking or catalytic reforming unit. The $H_2$/hydrocarbon molar ratio at the inlet of reactor 8 is from 1 to 4 and preferably from 1.5 to 2.5.

In the stabilization column 19, there is essentially separated a gasoline fraction of high isooctane content, discharged through line 21, which may be used as premium gasoline (a portion may be recycled through duct 23 to the hydrogenation zone 8), and a gasoline fraction of high isododcane content, discharged through duct 22 (a portion may be recycled through duct 24 to the hydrogenation zone 8).

The catalyst used for hydrogenation may be either a catalyst based on nickel or a catalyst making use of a noble metal or a mixture of noble metals as active gents; in the latter case, it is preferred to use palladium or platinum. In any case, the hydrogenation catalyst carrier must be a non-acidic carrier so as to avoid parasitic polymerization reactions resulting in the formation of gums which foul the catalyst. Among the carriers which can be used, according to the invention are silica, aluminas of low specific surface (from 10 to 90 $m^2/g$), and the nickel or cobalt aluminates prepared, for example, by impregnating $\gamma$-cubic alumina with 5 to 10% of nickel or cobalt oxides introduced, for example, as nitrates, and then calcining the so-impregnated carrier at a temperature from 800° to 900° C.

The first fraction, discharged through duct 5 from the fractionation zone 4, is fed to the alkylation zone 25.

As a rule, the alkylation reaction is effected in the presence of a solid catalyst as a fixed bed, or in the presence of a dissolved catalyst, i.e. in liquid phase, at a temperature from $-20°$ to $+200°$ C., under a pressure from 0.1 to 200 atmospheres. The operation may thus be effected in liquid phase in the presence of a strong inorganic acid such as hydrofluoric acid or sulfuric acid with or without addition of a Lewis acid such as boron trifluoride or antimony pentafluoride, or aluminum trichloride, and/or in the optional presence of a Bronsted acid. The operation may also be effected in vapor phase, in the presence of a solid catalyst of the following types: phosphates, arseniates or stannates of polyvalent metals with added boron trifluoride. Other available alkylation processes are effected in the presence of catalysts with a zeolite molecular sieve structure, with or without, for example, silicaaluminas, optionally with at least one metal such as nickel, palladium, rhodium, platinum and the like.

The alkylation reaction is effected, in particular, at temperatures close to room temperature and at moderate pressures.

There is thus obtained, by alkylation, an alkylate which is discharged through duct 26 and which may be fractionated in zone 27, so as to obtain:

LPG, discharged through duct 28, comprising mainly saturated hydrocarbons (iso- or normal paraffins) with 3 or 4 carbon atoms per molecule, an optional fraction of high isobutane content, discharged through duct 29, which may be recycled to the alkylation zone 25, or which may be used to dilute the charge, supplied to the polymerization an alkylate of high isooctane content to be used, for example, as motor gasoline, discharged through duct 30, and optionally a residue of small volume, which is discharged through duct 31.

LPG from duct 28 is fed to a separation zone 32 to recover, through duct 33, hydrocarbons with 3 and less than 3 carbon atoms per molecule, and through duct 34, butane, this butane fraction being optionally fed through duct 35 to dilute the charge of duct 1 when it contains more than 35% of by weight of isobutene. A portion of butane may also be usefully recycled to the cracking zone from which is recovered the olefinic cut which is treated according to the invention. The recycled butane fraction, in the polymerization zone 2, represents advantageously from 5 to 10% by weight of the olefinic cut or charge to be treated.

EXAMPLE

The feed charge to be treated has been obtained by diluting an olefinic $C_4$ cut with a mixture of butane and isobutane; the composition of this charge is given in Table I.

TABLE I

| COMPOSITION OF THE FEED CHARGE (% by weight) | |
|---|---|
| propane | 0.8 |
| isobutane | 34.9 |
| butane | 9.1 |
| isobutene | 17.1 |
| 1-butene | 14.0 |
| 2-butene (trans) | 13.9 |
| 2-butene (cis) | 8.6 |
| butadiene | traces |
| isopentane | 0.8 |
| pentenes | 0.8 |

The charge is treated in a polymerization zone (zone 2 of the figure).

The operating conditions are:
VVH $(h^{-1})$ 2
T °C. 150
P bars 40

The fixed bed catalyst consists of silica-alumina of the Trade, Durabead Perl Catalysator Neu type from Kalichemic Company.

The composition of the resultant products at the outlet of the polymerization zone is given in Table II:

TABLE II

| COMPOSITION OF THE POLYMERIZATION EFFLUENT (% by weight) | |
|---|---|
| propane | 0.8 |
| isobutane | 33.8 |
| butane | 9.1 |
| isobutene | 1.7 |
| 1 and 2-butenes | 33.4 |
| butadiene | — |
| $C_8$ olefins | 15.4 |
| $C_{12}$ olefins | 5.4 |
| $C_5^+$ paraffins | traces |
| $C_{12}^+$ | 0.4 |

Propane, isobutane, butane, isobutene and 1- and 2-butenes are collected in line 5 of the figure. This fraction is passed to the alkylation zone 25 where it is treated conventionally in the presence of hydrofluoric acid. The recovered butane and isobutane are partly used to dilute the feed charge, to the polymerization zone said composition of the charge being given in Table I.

The $C_8$ olefins, the $C_{12}$ olefins and the $C_{12}^+$ are conveyed, through ducts 6 and 7, to the hydrogenation zone 8. In the latter zone, the fixed bed catalyst contains 0.3% by weight of palladium on alumina having a 60 $m^2g^{-1}$ specific surface and a 0.5 cc/g pore volume. The operating conditions are as follows:

VVH $(h^{-1})$:1.5(fresh diluted charge)(initial charge)
T °C:200
P bars:40
$H_2$/HC (moles):1(fresh diluted charge)(initial charge)
Liquid recyle rate:6

Table III gives the composition of the charge before hydrogenation and that of the products obtained by hydrogenation. The polymerizate, before hydrogenation, is analysed by first lowering the temperature of the hydrogenation reactor down to room temperature (20° C.) the hydrogen supply being interrupted; the composition of the product is then determined both in the liquid phase and the vapor phase.

TABLE III

Hydrogenation of the fraction of the polymerization effluent. Composition of the charge and the product in % by weight

| COMPOSITION | CHARGE (line 6 of figure) | PRODUCT (line 9 of figure) |
|---|---|---|
| $C_8^-$ olefins | 2.1 | — |
| $C_8$ olefins | 71.1 | — |
| $C_{12}$ olefins | 24.9 | — |
| $C_{12}^+$ | 1.9 | — |
| $C_8^-$ paraffins | — | 2.2 |
| $C_8$ paraffins | — | 70.5 |
| $C_{12}$ paraffins | — | 24.6 |
| $C_{12}^+$ paraffins | — | 1.7 |

The $C_8$ and/or $C_{12}$ paraffinic components may be used as gasoline, in admixture with at least a portion of the alkylate obtained from line 30 of the figure.

What we claim is:

1. A process for producing an alkylate and gasoline of high isooctane content from an olefinic cut consisting essentially of $C_4$ hydrocarbons recovered from a cracking unit effluent, said process comprising the steps of:

(a) feeding the olefinic $C_4$ cut to a catalytic polymerization zone, wherein the catalyst consists essentially of silica-alumina, and converting therein at least 90% of the isobutene contained in the cut, the aggregate conversion of the normal butenes contained in the cut being kept lower than 10%;

(b) fractionating the effluent from the polymerization zone in a fractionation zone and recovering therefrom (i) a fraction comprising in major part isobutene dimers and trimers, and (ii) a fraction comprising in major part isobutane, butane and butenes;

(c) feeding fraction (i) from step (b) to a catalytic hydrogenation zone, hydrogenating said fraction therein and recovering therefrom an effluent consisting essentially of an isooctane fraction and an isododecane fraction; and (d) feeding fraction (ii) from step (b) to an alkylation zone and effecting an alkylation of said fraction therein, fractionating the resultant effluent, and recovering therefrom (iii) an alkylate gasoline fraction of high isooctane content, and (iv) a fraction consisting essentially of hydrocarbons with not more than 4 carbon atoms per molecule.

2. A process according to claim 1, wherein the olefinic $C_4$ cut comprises more than about 35% by weight of isobutene, and said cut is diluted with at least one portion of at least one of butane and isobutane recovered from the effluent of the alkylation zone, the resultant diluted cut being supplied as the charge to the polymerization zone.

3. A process according to claim 2, wherein the portion of at least one of butane and isobutane used to dilute the olefinic cut to be treated represents from 5 to 10% by weight thereof.

4. A process according to claim 1, wherein the carrier of the hydrogenation catalyst is selected from silica, aluminas of a specific surface lower than 100 $m^2/g$ and nickel and cobalt aluminates.

5. A process according to claim 1, wherein the effluent from the hydrogenation zone obtained in step (c) is further fractionated to obtain a gasoline fraction of high isooctane content suitable for use as a premium gasoline, and a gasoline fraction of high isododecane content.

6. A process according to claim 1, which further comprises the step of feeding fraction (iv) from step (d) to a separation zone and recovering therefrom a fraction consisting essentially of hydrocarbons with not more than 3 carbon atoms per molecule, and a butane fraction.

7. A process according to claim 5, wherein at least a portion of at least one of said isooctane and isododecane fractions obtained from the hydrogenation zone effluent is admixed as gasoline with at least one portion of the alkylate of high isooctane content obtained in the alkylation zone.

8. A process according to claim 6, wherein at least a portion of said butane fraction is recycled to the cracking zone from which the olefinic cut has been recovered.

9. A process according to claim 1, wherein the silica content of the silica-alumina polymerization catalyst is from 60 to 95% by weight.

10. A process according to claim 9, wherein said silica content is from 70 to 90% by weight.

11. A process according to claim 1, wherein the polymerization step (a) is effected at a temperature of from 100° to 180° C., a pressure of from 25 to 60 bars, and a space velocity of from 0.5 to 5 liters of feed per liter of catalyst per hour.

12. A process according to claim 6, wherein a portion of said butane fraction is used to dilute the olefinic $C_4$ cut supplied to the polymerization zone.

13. A process according to claim 1, which further comprises recovering from the fractionation of the alkylation effluent a fraction of high isobutane content.

14. A process according to claim 13, wherein a portion of said fraction of high isobutane content is used to dilute the olefinic $C_4$ cut supplied to the polymerization zone.

* * * * *